United States Patent
Englehart

(10) Patent No.: US 8,515,552 B2
(45) Date of Patent: Aug. 20, 2013

(54) METHOD OF ALLEVIATING MOTION SICKNESS

(75) Inventor: Krystle Jo Englehart, Pittsburgh, PA (US)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 13/502,801

(22) PCT Filed: Sep. 15, 2010

(86) PCT No.: PCT/IB2010/054168
§ 371 (c)(1),
(2), (4) Date: Apr. 19, 2012

(87) PCT Pub. No.: WO2011/051831
PCT Pub. Date: May 5, 2011

(65) Prior Publication Data
US 2012/0203309 A1   Aug. 9, 2012

Related U.S. Application Data

(60) Provisional application No. 61/255,653, filed on Oct. 28, 2009.

(51) Int. Cl.
*A61N 1/00* (2006.01)

(52) U.S. Cl.
USPC ........................................... 607/76

(58) Field of Classification Search
USPC ............................. 607/76, 59, 63
See application file for complete search history.

(56) References Cited

U.S. PATENT DOCUMENTS

| | | | |
|---|---|---|---|
| 6,314,324 | B1 | 11/2001 | Lattner et al. |
| 6,748,275 | B2 | 6/2004 | Lattner et al. |
| 2007/0167985 | A1 | 7/2007 | Kirby |
| 2007/0173908 | A1* | 7/2007 | Begnaud .................. 607/63 |
| 2009/0082831 | A1* | 3/2009 | Paul et al. ................ 607/59 |

* cited by examiner

*Primary Examiner* — George Manuel
*Assistant Examiner* — Robert N Wieland
(74) *Attorney, Agent, or Firm* — Timothy A. Nathan

(57) ABSTRACT

The present invention provides a method of alleviating motion sickness in a patient during a predetermined event. The predetermined event commencing at a start time. The patient having a vestibular system. The method including determining the start time of the predetermined event. The method further including providing a stimulus to the vestibular system of the patient during a treatment, the treatment occurring a predetermined amount of time before the start time of the predetermined event and lasting a predetermined duration.

14 Claims, 3 Drawing Sheets

METHOD OF ALLEVIATING MOTION SICKNESS

The present invention relates generally to the treatment of a patient to regulate one or more physiological and/or psychological functions controlled by the hypothalamus by means of vestibular stimulation. More particularly, the present invention relates to a method of alleviating motion sickness in a patient during a predetermined event by providing a number of vestibular stimulation treatments to the patient prior to the predetermined event.

Motion sickness or kinetosis, also known as travel sickness, is a condition in which a disagreement exists between a person's visually perceived movement and the movement sensed by the person's vestibular system. Depending on the cause, it may also commonly be referred to as seasickness, car sickness, simulation sickness, airsickness, or space sickness. Common symptoms of motion sickness include dizziness (vertigo), nausea and fatigue.

It is believed that roughly 33% of people are susceptible to motion sickness even in mild circumstances such as being on a boat in calm water, although nearly 66% of people are susceptible in more severe conditions. As an example, approximately 50% of the astronauts in the U.S. space program have suffered from space sickness. Individuals and animals without a functional vestibular system have been found to be immune to motion sickness.

Motion sickness on the sea can result from being in the berth of a rolling boat without being able to see the horizon. Sudden jerky movements tend to be worse for provoking motion sickness than slower smooth ones, because such movements tend disrupt the fluid balance in the vestibular system more. For example, a "corkscrewing" boat will tend to upset more people than one that is gliding smoothly across the oncoming waves. Cars driving rapidly around winding roads or up and down a series of hills will tend to upset more people than cars that are moving over smooth, straight roads. Looking down into one's lap to consult a map or attempting to read a book while a passenger in a car may also bring on motion sickness. Similarly, travel in a commercial jetliner, where the ability to see outside the cabin is limited/restricted, can commonly cause motion sickness, even more so when turbulent conditions are encountered.

Many "cures" and preventatives for motion sickness have been proposed having varying degrees of effectiveness and associated drawbacks. One common treatment suggestion is to simply look out of the window of the moving vehicle and to gaze toward the horizon in the direction of travel. Such action helps to re-orient the inner sense of balance by providing a visual reaffirmation of the motion sensed by the vestibular system. However, such solution is not always effective and/or available, such as when travelling in a commercial jetliner, as previously discussed, or in a ship without windows.

Over-the-counter and prescription medications are readily available for treating symptoms of motion sickness. However, many pharmacological treatments which are effective for nausea and vomiting in some medical conditions may not be effective for motion sickness. For example, metoclopramide and prochlorperazine, although widely used for nausea, are ineffective for motion-sickness prevention and treatment. This is due to the physiology of the CNS vomiting centre and its inputs from the chemoreceptor trigger zone versus the inner ear. Sedating anti-histamine medications such as promethazine work quite well for motion sickness, although they can cause significant drowsiness.

Electronic treatments for motion sickness have also been studied. As astronauts frequently have motion sickness, NASA has done extensive research on the causes and treatments for motion sickness. One such electronic treatment involves the person suffering from motion sickness to wear LCD shutter glasses that create a stroboscopic vision.

Although there are many known methods for treating motion sickness, such methods still leave room for improvement.

In one embodiment, the invention provides a method of alleviating motion sickness in a patient having a vestibular system during a predetermined event commencing at a start time. The method includes determining the start time for the predetermined event and providing a stimulus to the vestibular system of the patient during a treatment. The treatment beginning a predetermined amount of time before the start time of the predetermined event and lasting a predetermined duration.

The method may further include determining a treatment schedule for the patient after determining the start time for the predetermined event and prior to providing a stimulus.

The stimulus may comprise an electrical stimulation provided by an electrical nerve stimulation device. The electrical stimulation may comprise a sinusoidal wave current stimulation output. The sinusoidal wave current stimulation output may have a frequency at or about 0.50 Hz. The sinusoidal wave current stimulation output may have a peak output of between 0.1 and 1.0 milliamps.

The predetermined amount of time may be between one and seven days before the predetermined event.

The duration may be about 30 minutes.

The treatment may be a first treatment, and the method may further include providing a stimulus to the vestibular system of the patient during a number of subsequent treatments occurring after the first treatment. Each of the number of subsequent treatments occurring a predetermined time before the start time of the predetermined event and each of the subsequent treatments lasting a predetermined second duration.

The predetermined event may be an event selected from the group consisting of: riding in an automobile, riding on a boat and riding in a plane.

The accompanying drawings illustrate exemplary embodiments of the invention, and together with the general description given above and the detailed description given below, serve to explain the principles of the invention. As shown throughout the drawings, like reference numerals designate like or corresponding parts.

As used herein, the term "patient" shall be used to refer to any person being subjected to the method described herein.

As used herein, the term "predetermined event" shall be used to refer to any event during which a patient may develop one or more symptoms of motion sickness. Such events may commonly include for example, without limitation, travelling in an automobile, airplane, or boat.

As used herein, the term "number" shall be used to refer to any nonzero quantity (i.e., one or more than one).

The present invention utilizes one or more vestibular stimulation treatments administered in advance of a motion sickness inducing event in order to alleviate motion sickness during the event. A detailed description of such treatment method is provided below.

Known systems and methods of vestibular stimulation are disclosed in U.S. Pat. Nos. 6,748,275 and 6,314,324 to Lattner et al. These patents disclose an apparatus and method in which the portions of the labyrinth associated with the labyrinthine sense and/or the nerves associated therewith are stimulated to: augment or control a patient's respiratory function, open the patient's airway, induce or promote sleep, counteract vertigo, or a combination of these functions. For example, the treatment of insomnia may be achieved by stimulating the vestibular system such that the patient perceives a gentle rocking sensation, generally equivalent to rocking a child to sleep.

The present inventor recognized that by manipulating the stimulation to the vestibular system of a patient, such rocking sensation may be tailored to closely mimic the rocking sensation experienced in a boat, car, airplane, etc. and thus induce feelings similar to motion sickness in a patient as if they were actually participating in such motion sickness causing event. Further, the present inventor recognized that after being subjected to such treatments for a period of time or successive number of treatments, the motion sickness-like symptoms experienced by the patient would dissipate and generally disappear as the patient adapted to the feelings associated with the treatment. Thus further treatments, or alternatively a typical motion sickness causing event, would tend to not produce symptoms of motion sickness in the treated patient. From such findings, the present inventor discovered that tailored vestibular stimulation treatments may be employed as a proactive treatment to alleviate motion sickness, as will be described below.

Figure 1:
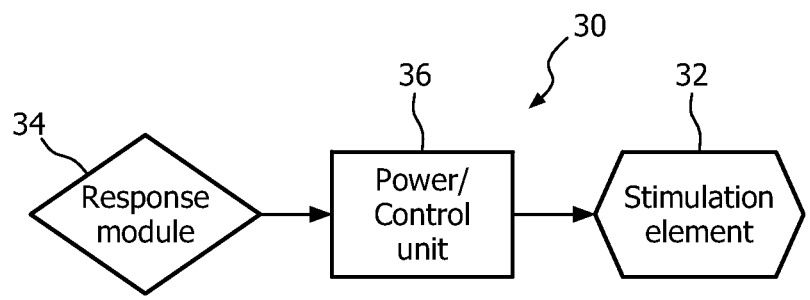
FIG. 1 is a schematic diagram of a vestibular stimulation system according to one embodiment of the present invention.

FIG. 1 schematically illustrates an exemplary embodiment of a vestibular stimulation system 30 that may be employed according to the principles of the present invention. Vestibular stimulation system 30 is a device that stimulates portions of the labyrinth associated with the labyrinthine sense and/or associated nerves to provide a therapeutic benefit to the patient. More specifically, the present invention contemplates stimulating, either invasively or more preferably non-invasively, the receptors of the labyrinth associated with the labyrinthine sense and/or the nerves or nerve branches associated with such receptors, including the saccule, utricle, semicircular canals, vestibular nuclei, vestibular nerve and its nerve branches.

The present invention contemplates providing stimulation to at least one of these stimulation sites to elicit a desired response from the hypothalamus of the patient. The desired response may include one or more physiological and/or psychological effects, as will be described below. However, a general description of the stimulation system of the present invention is first provided. It should be noted that the stimulation system of the present invention is referred to throughout the present disclosure as a "vestibular stimulation system" because the stimulation sites of interest in the present invention are the above-identified structures and/or tissues of the human inner ear associated with the labyrinthine sense, which is commonly referred to as the vestibular system.

As shown in FIG. 1, vestibular stimulation system 30 preferably includes the following three components: a stimulation element 32 that performs the actual stimulation of the tissue, a response module 34 to monitor a response of the patient's hypothalamus, and a power/control unit 36 that receives the signals provided by response module 34 and causes stimulation energy to be provided to stimulation element 32 at an appropriate timing, level, pattern, and/or frequency to achieve the desired physiological function.

Stimulation element 32 may be any device or combination of devices that provides a controlled stimulation to a target site. As noted above, the particular stimulation sites of interest in the present invention are one or more of the following and/or a combination thereof: the vestibular nerve, portions of the vestibular nerve, the branches of vestibular nerve or portions thereof, each of the semicircular canals (anterior, posterior, and lateral) or portions thereof, the common limb, utricle, saccule, and ampullae. It is to be understood that the precise stimulation site or sites, as well at the method in which the sites are stimulated, will vary depending on the desired response of the hypothalamus to be achieved.

Stimulation of each of these tissues can be provided on the surface, internally, or in nearby tissues or structures. In addition, depending on the stimulation technique used, the stimulation devices can be completely invasive, completely non-invasive, or a combination thereof.

The present invention contemplates stimulating one or more of the above stimulation sites using one or more of a variety of stimulation techniques, such as electrical, mechanical, magnetic, thermal, chemical, radio frequency, or infrared stimulation. The specific mechanism or combination of mechanisms for delivering the stimulation will depend on the stimulation technique used, which will depend on the stimulation site selected. The following are examples of suitable stimulation techniques and their stimulation mechanism that can be used in the vestibular stimulation treatment method of the present invention to stimulate one or more of the stimulation sites identified above.

Electrical Stimulation—The present invention contemplates providing electrically conductive electrodes in, on, and/or near the tissue to be stimulated so that an electric current can be delivered to the adjacent tissue via the electrode. The electrodes can be invasive, non-invasive, or a combination thereof. The electrodes can be placed near the vestibular system and/or at other locations on the patient, such as the forehead, so long as a stimulation energy is delivered to the patient's vestibular system. The electrode or electrodes can have a variety of sizes and configurations depending on the stimulation pattern to be provided. For example, a point electrode can be used to stimulate a very specific site, or a spot or strip electrode can be provided to induce stimulation over a larger area. U.S. Appln. Pub. No. 2007/0167985 discloses an "ear bud" type of stimulation electrode suitable for use in the present invention, in which the electrode is situated in the ear canal.

The present invention further contemplates providing electrical stimulation using a current controlled source, in which the current output to the electrode is monitored. The current source automatically adjusts the current to keep it at or near the desired current level if, for example, the resistance of the patient changes.

Additionally, the present invention contemplates using a microstimulator electrode that is inserted at the stimulation site and that receives power and control data from an external source, such as an rf field created by an external oscillator.

A specific type of a strip electrode that can be used in the present invention to stimulate a nerve is an electrode cuff that completely or partially surrounds a nerve or nerve branch to be stimulated. Because the cuff surrounds to target nerve, it allows the stimulation energy to be delivered through the nerve tissue while minimizing collateral stimulation of other tissues. Of course, multiple electrodes and electrode pairs can be provided to achieve the desired stimulation pattern over the desired area to be stimulated. In addition, the present invention contemplates inserting one or more needle electrodes into the inner ear for selective simulation of a nerve, nerve branch, or a global area, such as the saccule, to promote the desired hypothalamic response. A needle electrode has the advantage of being able to target a specific location for stimulation.

Mechanical Stimulation—The present invention contemplates placing a pressure application device, such as an inflatable balloon, near the tissue to be stimulated so that inflating the balloon applies a pressure on the adjacent tissue. This type of mechanical stimulation system provides pressure fluctuations to the patient to promote a particular sensation. Another example of a pressure application device particularly well suited for use with the semicircular canal or with a nerve is a pressure cuff, which is placed either completely or partially around the canal or nerve to be stimulated so that inflating the pressure cuff exerts pressure on the underlying portion of the semicircular canal or nerve. Yet another mechanical stimulation device is a vibrating element that produces a mechanical vibration at a selected frequency.

Sonic Stimulation—The present invention also contemplates stimulating the vestibular area or specific sites within this area using a sonic or ultrasonic device that delivers stimulation on a carrier wave typically above 20,000 Hz, which is not in the audible range for humans.

Magnetic Stimulation—The present invention further contemplates providing a magnetic field generator in the form of one or more coils in and/or near the inner ear. The coils generate a time varying magnetic field that creates a spatially varying electric field that induces stimulation in the target tissue. In addition, focusing elements, such as ferromagnetic material implants, can be provided in or near the targeted tissue to focus or shape the magnetic field, and, hence the electric field, at a specific location.

Thermal Stimulation—The present invention contemplates providing a stimulation device that uses changes in temperature to induce stimulation of the patient's tissue. Examples of devices that induce a temperature change include a laser, infrared device, or a device that dispenses heated or chilled liquid to the stimulation site.

Chemical Stimulation—The present invention further contemplates providing a device that introduces chemicals or that causes chemical reactions at a stimulation site to control the stimulation at that site. For example, an injection or medicine pump can be provided at the inner ear to introduce the desired stimulation medication at the stimulation site.

Radio-Frequency (RF) Stimulation—The present invention still further contemplates using radio frequency wavelengths generated by a suitable device to provide the desired stimulation. For example, as noted above, stimulation can be induced by providing power and control data using radio frequencies (RF) received by one or more microstimulators implanted in the patient. Different microstimulators implanted at different locations in the patient can be tuned to different frequencies so that a wide variety of stimulation patterns can be achieved.

Infrared Stimulation—The present invention also contemplates using infrared technology to deliver the stimulation to the patient's tissues. Short wave, 7,200-15,000 .ANG., or long wave, 15,000-150,000 .ANG., systems can be used to deliver the stimulation to the target site.

It is to be understood that the list of stimulation techniques provided herein is not exhaustive or exclusive. On the contrary, the present invention contemplates using any stimulation technique or device that, when actuated, provides the desired stimulation function and pattern as described below. The selection and different types of suitable stimulation devices suitable for use in achieving the desired physiological function of the present invention will be better understood from the discussion of the particular implementations of the stimulation system of the present invention provided below.

Figure 2:
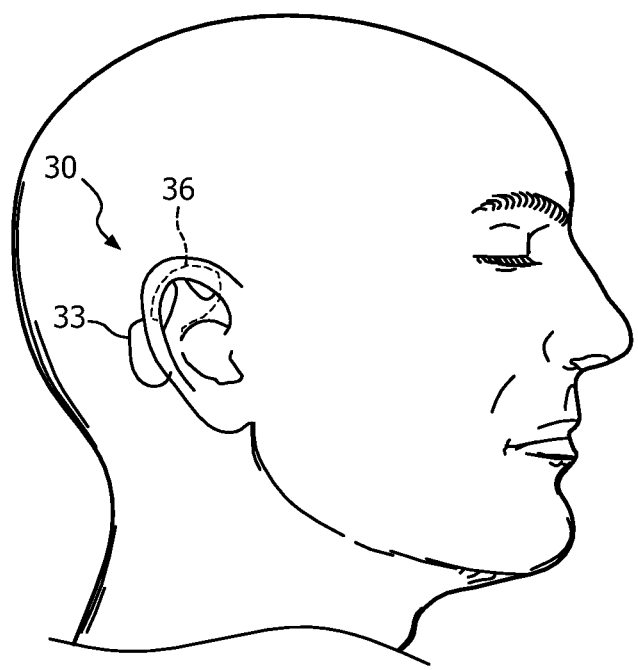
FIG. 2 is a side view of a human head showing the positioning of a non-invasive vestibular stimulation system using surface electrodes as a stimulating element according to one embodiment of the present invention.
Figure 3:
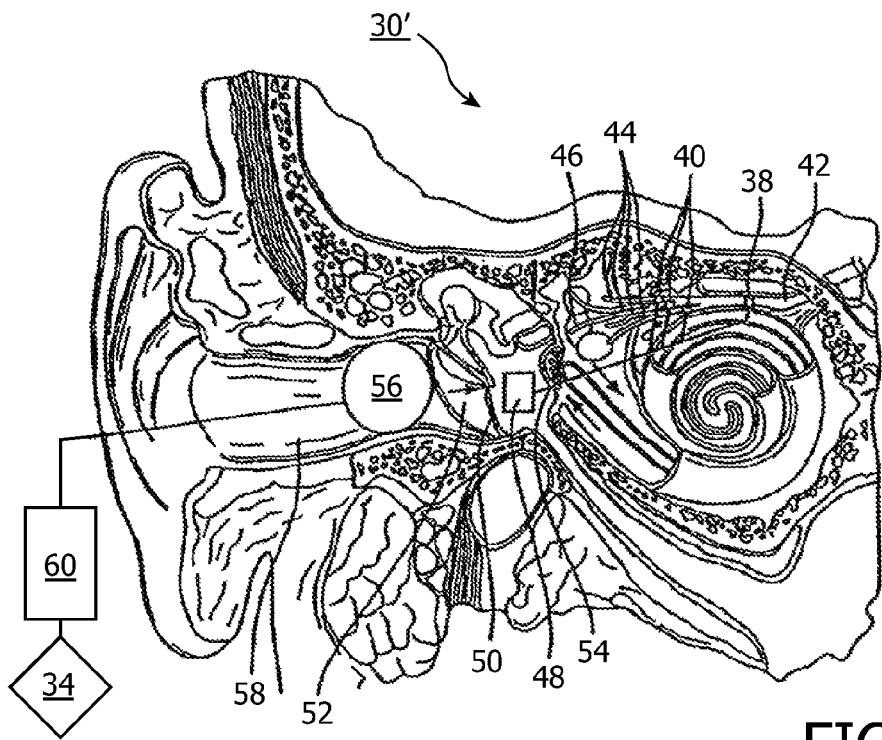
FIG. 3 is a sectional view of a portion of the human anatomy showing the inner ear and schematically showing an invasive vestibular stimulation system according to one embodiment of the invention.
Figure 4:
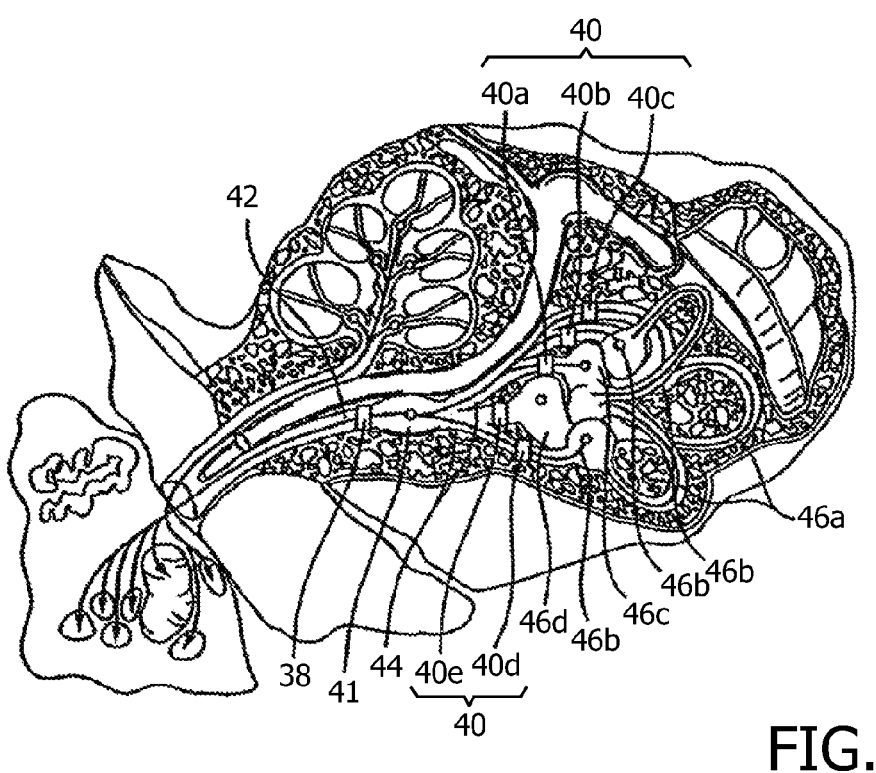
FIG. 4 is a sectional view of a portion of the human anatomy also showing the inner ear and schematically showing the location of stimulation electrodes on the vestibular nerve and nerve branches, in accordance with one embodiment of the invention.

FIGS. 2, 3, and 4 illustrate exemplary embodiments of vestibular stimulation systems 30. Referring to FIG. 2, vestibular stimulation system 30 is a completely non-invasive system in that no part of the system is disposed in the patient. It is to be noted that placing a portion of the system, such as the stimulation electrode, in the ear canal is considered to be non-invasive as such portion may be readily inserted and removed without any deleterious effects to the patient. Vestibular stimulation system 30 in FIG. 2 includes a stimulation element 33 in the form of a surface electrode that, in this exemplary embodiment, is disposed on the surface of the patient just behind the ear so that the electrode generally overlies the vestibular system. The remaining portions of the stimulation system, such as the power supply and the control unit 36, are worn on the ear in the same manner as a conventional hearing aid. When activated, the power supply and control unit 36 energize electrode 33 to send a stimulating current to the patient's vestibular system. An example of such an electrical vestibular stimulation system 30 of FIG. 2 is the VirtuSom™ device manufactured and sold by Philips Respironics of Monroeville, Pa.

FIG. 3 shows an example of an invasive vestibular stimulation system 30' that directly stimulates the vestibular nerve and/or its branches. It is considered invasive because at least a portion of the system is disposed internal to the patient. Vestibular stimulation system 30' includes stimulation elements 38 and 40, which are electrodes placed directly on or near vestibular nerve 42 and/or branch nerves 44 that lead to the vestibular nerve. The present invention contemplates that electrodes 38 and/or 40 can be positioned relative to the vestibular nerve 38 and/or a branch nerves 44 associated therewith, respectively, at a variety of locations along these nerves or nerve branches, so long as they are positioned so as to induce stimulation in the associated nerve. For example, electrode 38 can be provided on vestibular ganglion 41. Branch nerves 44 are the nerves coupled to the receptors of the labyrinth associated with the labyrinthine sense, such as the semicircular canals 46a, ampullae 46b, utricle 46c, and saccule 46d. Note that the semicircular canals, ampullae, utricle, and saccule are generally identified by numeral 46 in FIG. 3, but are shown in greater detail in FIG. 4. Branch nerves 44 combine to form vestibular nerve 42.

FIG. 4 illustrates in better detail the inner ear and the placement of electrodes 40a-40e on branch nerves 44 and the placement of electrode 38 on vestibular nerve 42. Electrodes 40a-40e are generally illustrated in FIG. 3 as electrodes 40. It is to be understood that the number of electrodes and their locations can vary and that electrode stimulators need not be placed on each branch nerve. For example, electrode 38 on vestibular nerve 42 or one or more electrodes 40a-40e on branch nerves 44 may be eliminated if the desired stimulation effect is achieved by stimulating another nerve or nerves. Ideally, the number of electrodes should be kept to a minimum while providing the desired stimulation effect.

Referring again to FIG. 3, in the illustrated exemplary embodiment, power/control unit 36 of vestibular stimulation systems 30' includes a signal receiving device 48 implanted in tympanic cavity 50 on the interior side of eardrum 52. A signal generator 56 is provided on the exterior side of eardrum 52 in ear canal 58. One or more leads 54 couple signal receiving device 48 to each of electrodes 38 and/or 40 so that each electrode can be energized individually or in any combination. For example, this configuration allows for simultaneous stimulation of multiple electrodes at multiple sites based on a common stimulation source from signal receiving device 48. In addition, this configuration allows for independent control of one or more of the electrodes to provide a great degree of flexibility for the different types of stimulation patterns that can be applied to the patient's vestibular system. For example, the present invention contemplates stimulating between sites, for example, from 40a to 40b, 40a to 40c, 40b to 40c, etc.

Signal generator 56 communicates with signal receiver 48 to cause signal receiver to provide stimulation energy to stimulation electrodes 38 and/or 40. In an exemplary embodiment of the present invention, signal generator 56 generates an electromagnetic field that induces a current in signal receiving device 48, which is then transmitted to electrodes 38 and/or 40. If, however, signal receiving device 48 is provided with its own power supply, the signals from signal generator 56 are command and control signals that dictate how and when the stimulation energy is output from signal receiving device 48. It should be noted that signal generator 56 need not be provided within the ear canal, as shown, if its transmission range is sufficient to transmit greater distances.

The present invention also contemplates doing away with signal receiving device 48 and leads 54 in favor of having an electromagnetic field produced by signal generator 56 directly induce stimulation pulses at the electrodes or at the stimulation site. For example, magnetic stimulation can be used to induce stimulation in the target tissue. In which case, the coil or coils that generate the magnetic field function as signal generator 56, and electrodes 38 and/or 40 can be eliminated. Alternatively, ferromagnetic devices that shape the fields generated by the can be provided at or near the stimulation sites to function in much the same capacity as electrodes 38 and/or 40 to ensure that the target site is adequately and properly stimulated.

The present invention also contemplates that one or more microstimulators, which receive power and data from an external source via RF frequencies, can be implanted in the patient to function as electrodes 38 and/or 40. In which case, the RF oscillator functions as signal generator 56 and is located externally relative to the patient, such as at the patient's bedside.

A power/control unit 60, similar if not identical in function to power/control unit 36 discussed above, causes signal generator 56 to produce the electromagnetic field or other coupling mechanism that initiates stimulation. In the illustrated embodiment, at least one sensor 34 communicates with power/control unit 60 to provide an input signal that is used by the control unit to determine when to generate the electromagnetic field.

As noted above, the present invention contemplates stimulating one or more locations in the inner ear associated with the labyrinthine sense, in addition to or in place of direct stimulation of the vestibular nerve and its branches, as shown in FIGS. 2, 3 and 4, in order to provide a therapeutic benefit. That is, it is not necessary that the vestibular nerve or its branches be directly stimulated in order to induce a neural transmission in the vestibular nerve. Because the vestibular nerve is an afferent nerve, and stimulating anything before it involves transduction, stimulation can be provided at one or more sites before the vestibular nerve and still induce the desired neural transmission therein. It should be noted that the term "before" as used in this paragraph refers to portions of the nerve in a direction opposite the direction of normal neural conduction.

Having thus described various examples of potential ways in which the vestibular system of a patient may be stimulated, a method 100 utilizing such stimulation for alleviating motion sickness in a patient during a predetermined event will now be described in conjunction with FIG. 5. The method 100 conditions a patient prior to the predetermined event (motion sickness causing event) by inducing in the patient motion sickness-like symptoms through vestibular stimulation such that the patient's body will be adapted to such effects prior to the predetermined event and thus not suffer, or at minimum suffer greatly reduced symptoms of motion sickness during the predetermined event.

Figure 5:
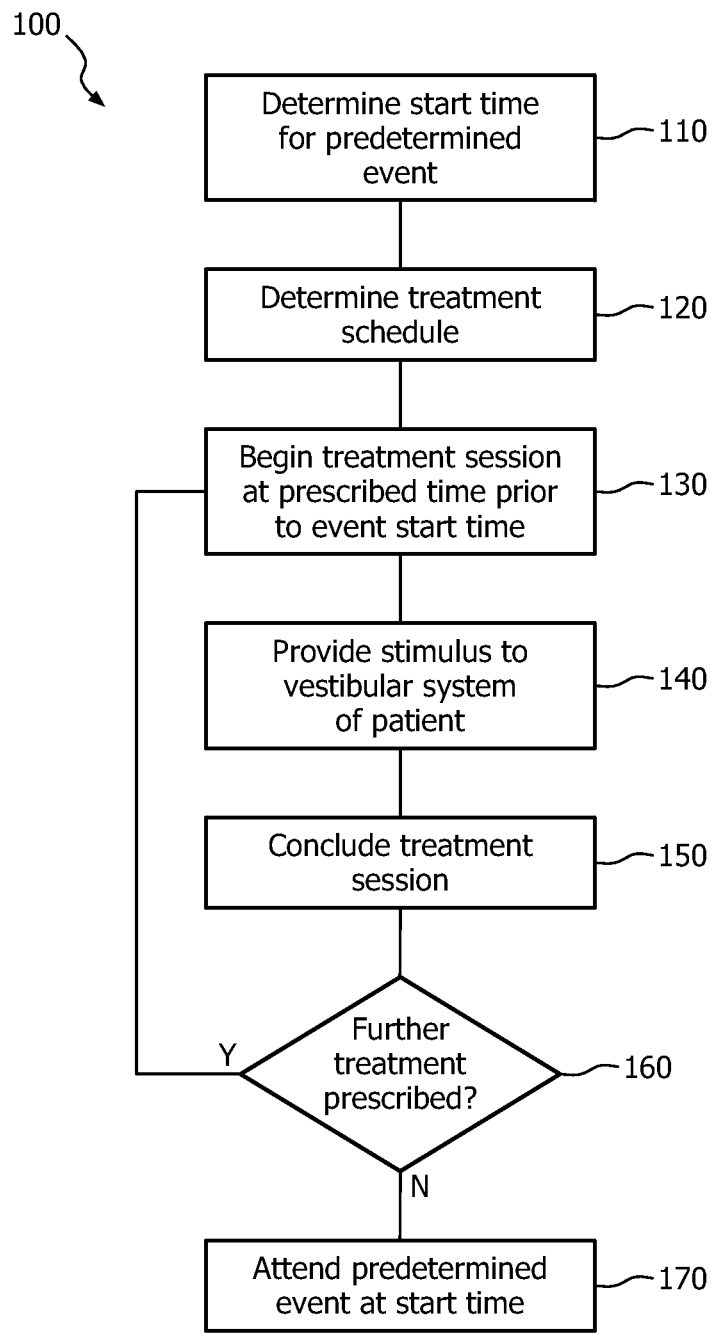
FIG. 5 is a flow chart depicting a method in accordance with an embodiment of the invention.

Referring to FIG. 5, the method 100 begins by determining 110 the start time for the predetermined event. For example, if a patient, referred to as Patient A, was going to be boarding a ship for a cruise scheduled to leave on September 1 at 1:00 pm, the cruise would be the predetermined event in which motion sickness-like symptoms would be encountered and 1:00 pm, September 1 would be considered the start time for the predetermined event.

Once the start time for the predetermined event has been determined at 110, a treatment schedule for the particular patient is determined 120. The treatment schedule generally includes the number of treatment sessions, the duration of each treatment session, and the timing of each of the number of treatment sessions with respect to the start time of the predetermined event. For example, without limitation, the treatment schedule for Patient A may include seven individual treatment sessions, each session lasting approximately thirty minutes and occurring once a day for the week prior to the September 1 departure for the cruise. It is to be appreciated that the susceptibility to motion sickness may vary tremendously from one patient to the next. Accordingly the treatment schedules, particularly the number and duration of treatments required, may vary from one patient to another. Generally optimum results for a particular patient are obtained through adjusting the treatment schedule for subsequent events based on feedback from the patient regarding previous treatments.

After the treatment schedule has been determined at 120 and during a treatment session provided according to the treatment schedule, a stimulus is provided 140 to the vestibular system of the patient. In an exemplary embodiment of the invention, the stimulus is provided by a non-invasive electrical stimulation device capable of providing a sinusoidal wave current stimulation output having a frequency of 0.5 Hz and a peak output generally in the range of 0.1 to 1.0 milliamps. An example of such device readily employed in such example is the VirtuSom™ device manufactured and sold by Philips Respironics of Monroeville, Pa. Ideally, each treatment session generally lasts the duration specified by the treatment schedule. However, the duration of each treatment session may be adjusted to better meet the potentially changing needs of the specific patient as the goal of each treatment session is to induce feelings of motion sickness, such as nausea, in order to condition the patient's body prior to the actual motion sickness inducing event. As such, in order to obtain optimum results, it is generally best for the patient to try to endure the treatment for as long as possible, up to the prescribed duration time.

Once the stimulus has been provided for the prescribed duration, the stimulus is removed and the treatment session is concluded 150. The treatment process is repeated according to the treatment schedule until it is determined 160 that no further treatment session is prescribed. After completing the treatment schedule the patient is then able to attend 170 the predetermined event with greatly minimized, if any, side effects due to motion sickness. Accordingly, the patient is able to better enjoy the predetermined event and not have to deal with the undesirable effects of motion sickness.

While embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

The invention claimed is:

1. A method of alleviating motion sickness in a patient caused by a predetermined event, the predetermined event commencing at a start time, the patient having a vestibular system, the method comprising:
   determining (110) the start time for the predetermined event; and
   providing (140) a stimulus to the vestibular system of the patient during a treatment alleviate motion sickness caused by the predetermined event, the treatment beginning a predetermined amount of time before the start time of the predetermined event and lasting a predetermined duration.

2. The method of claim 1 further comprising determining (120) a treatment schedule for the patient after determining (110) the start time for the predetermined event and prior to providing (140) a stimulus.

3. The method of claim 1 wherein the stimulus comprises an electrical stimulation provided by an electrical nerve stimulation device.

4. The method of claim 3 wherein the electrical stimulation comprises a sinusoidal wave current stimulation output.

5. The method of claim 4 wherein the sinusoidal wave current stimulation output has a frequency at or about 0.50 Hz.

6. The method of claim 4 wherein the sinusoidal wave current stimulation output has a peak output of between 0.1 and 1.0 milliamps.

7. The method of claim 1 wherein the predetermined amount of time is between one and seven days before the predetermined event.

8. The method of claim 1 wherein the duration is about 30 minutes.

9. The method of claim 1 wherein the treatment is a first treatment, the method further comprising:
   providing a stimulus to the vestibular system of the patient during a number of subsequent treatments occurring after the first treatment, wherein each of the number of subsequent treatments occur a predetermined time before the start time of the predetermined event and each of the subsequent treatments last a predetermined second duration.

10. The method of claim 1 wherein the predetermined event is an event selected from the group consisting of: riding in an automobile, riding on a boat and riding in a plane.

11. The method of claim 1, wherein the treatment begins before the patient feels symptoms of motion sickness.

12. The method of claim 1, wherein the treatment ends before the start time of predetermined event.

13. The method of claim 1, wherein providing the stimulus to the vestibular system of the patient during the treatment induces a rocking sensation in the patient.

14. The method of claim 13, wherein the rocking sensation causes symptoms of motion sickness in the patient.

* * * * *